United States Patent
Salzer et al.

(10) Patent No.: US 6,743,935 B2
(45) Date of Patent: Jun. 1, 2004

(54) PROCESS FOR THE PREPARATION OF RUTHENIUM COMPOUNDS

(75) Inventors: Albrecht Kurt Lutz Salzer, Aachen (DE); Frank Peter Herbert Podewils, Düsseldorf (DE); Stefan Geyser, Hueckelhoven (DE)

(73) Assignee: Firmenich SA, Geneva (CH)

( * ) Notice: Subject to any disclaimer, the term of this patent is extended or adjusted under 35 U.S.C. 154(b) by 7 days.

(21) Appl. No.: 10/265,743

(22) Filed: Oct. 8, 2002

(65) Prior Publication Data

US 2003/0032828 A1 Feb. 13, 2003

Related U.S. Application Data

(63) Continuation of application No. PCT/IB01/00784, filed on May 4, 2001.

(30) Foreign Application Priority Data

May 16, 2000 (EP) .............................................. 00110429

(51) Int. Cl.$^7$ ................................................ C07F 15/00
(52) U.S. Cl. ....................... 556/136; 549/512; 549/513; 549/554
(58) Field of Search .......................... 556/136; 549/513, 549/512, 554

(56) References Cited

U.S. PATENT DOCUMENTS 5,728,890 A * 3/1998 Hamamoto et al. .......... 568/361
6,342,621 B1 * 1/2002 Mukerjee et al. ............. 556/21

OTHER PUBLICATIONS

David N. Cox et al., XP–002147842 "Octadienediyl Dichlorides of Ruthenium (iv) as Synthetic Reagents in Organoruthenium Chemistry; Isolation of a Protonated "Open Metallocene, [Ru($\eta^5$–C$_7$H$_{11}$)$_2$H][BF$_4$], J. Chem. Soc., Chem., Comm. Vo. No.14, pp 951–953 (1988).

Lothar Stahl et al., XP–000946340, Synthesis and Characterization of Bis(pentdienyl)ruthenium Compounds. Organometallics, vol. 2, No. 9, pp 1229–1234 (1983).

Toerien et al., Bis(allyl) Ruthenium(iv) Complexes, Part 1, Synthesis of complexes containing Four–membered Ruthenium Heterocycles, Crystal Structure of [Ru($\eta^3$:$\eta^3$–C$_{10}$H$_{16}$)–(SN C$_7$H$_4$S–2)Cl], J. Chem. Soc., Dept. of Chem., Univ. of Pretoria, South Africa, pp. 1563–1568 (1991).

David N. Cox et al., (2,7–Dimethyloctadienediyl)ruthenium(IV) Complexes: Isomerism and Solution Equilibria for Dichlorobis ($\mu$–cholor)bis1–3–$\eta$:6–8–$\eta$)–2, 7–dimethyloctadienediyl}diruthenium(IV) and Related Monomeric Solvates, Inorg. Chem. Vo. 29, pp. 1360–1365 (1990).

"Formation of Dichloro(2,7–Dimethyl–Octa–2, 6–Diene 1, 8–Diyl)Ruthenium (IV) From RuCl$_3$ and Isoprene", Tetrahedron Letters, No. 47, pp. 4187–4189, Pergamon Press Ltd.

* cited by examiner

Primary Examiner—Peter O'Sullivan
(74) Attorney, Agent, or Firm—Winston & Strawn LLP

(57) ABSTRACT

A process for the preparation of ruthenium compounds of the formula {Ru(dienyl)$_2$} wherein "dienyl" represents a substituted pentadienyl or cycloheptadienyl group by reacting dichloro(2,7-dimethylocta-2,6-dien-1,8-diyl)-ruthenium with an appropriate diene in the presence of a primary or secondary alcohol capable of reducing Ru(IV) to Ru(II); and a carbonate of an alkaline material. These ruthenium compounds are useful as precursors of Ru catalysts.

7 Claims, No Drawings

PROCESS FOR THE PREPARATION OF RUTHENIUM COMPOUNDS

CROSS-REFERENCE TO RELATED APPLICATIONS

This application is a continuation of the US national phase designation of International application PCT/IB01/00784 filed May 4, 2001, the entire content of which is expressly incorporated herein by reference thereto.

TECHNICAL FIELD

The present invention relates to the preparation of ruthenium compounds useful as precursors of ruthenium catalysts. It concerns more particularly a process for the preparation of a ruthenium compound of formula {Ru(dienyl)$_2$}   (I)

wherein "dienyl" represents a substituted pentadienyl or cycloheptadienyl group.

PRIOR ART

A compound of the invention, bis(2,4-dimethyl-2,4-pentadienyl)-ruthenium or {Ru(DMPD)$_2$}, is a known product useful for the preparation of a great number of ruthenium catalysts, in particular compounds useful in asymmetric catalysis. Although a prior synthesis of this compound has been described by L. Stahl et al. In Organometallics 1983, 2, 1229–1234, practical working of this known process showed that it is not useful for industrial exploitation as it provides the desired compound in low yields, below 40%

SUMMARY OF THE INVENTION

In order to overcome the limitation of the prior art process, the invention relates more particularly to a new process for the preparation of a ruthenium compound of formula {Ru(dienyl)$_2$}   (I)

wherein "dienyl" represents a substituted pentadienyl or cycloheptadienyl group, which process comprises reacting dichloro(2,7-dimethylocta-2,6-dien-1,8-diyl)-ruthenium with an appropriate diene in the presence of:

1) a primary or secondary alcohol capable of reducing Ru(IV) to Ru(II); and
2) a carbonate of an alkaline metal.

DETAILED DESCRIPTION OF THE PREFERRED EMBODIMENTS

By "an appropriate diene" it is meant here the diene which, for a particular compound (I), provides the corresponding dienyl group.

According to a preferred embodiment of the invention the reaction is carried out in the presence of a catalytic amount of acetonitrile.

The process of the invention is particularly useful for preparing compounds (I) wherein "dienyl" stands for a 2,4-dimethyl-2,4-pentadienyl, 2,3,4-trimethyl-2,4-pentadienyl, 2,4-dimethyl-1-oxa-2,4-pentadienyl or 2,4-cycloheptadienyl group.

Dichloro(2,7-dimethylocta-2,6-dien-1,8-diyl)-ruthenium, used as the starting compound in the process of the invention, is a known compound. Several synthesis of this compound have in fact been described, e.g. by L. Porri et al., Tetrahedron Lett. 1965, 4187–4189, D. N. Cox et al., Inorg. Chem. 1990, 29, 1360–1365 and J. G. Toerien et al., J. Chem Soc. Dalton Trans. 1991, 1563–1568. However, to our knowledge, there has never been any report or suggestion of the use of this known compound for the preparation of compounds of formula (I).

Primary or secondary alcohols suitable for use in the process of the invention include ethanol, methanol and isopropanol, amongst other. Preferably, ethanol will be used.

Carbonates of alkaline metals appropriate for the process of the invention include lithium, sodium, and potassium carbonates in particular. Preferably lithium carbonate will be used.

According to an advantageous embodiment of the invention, dichloro(2,7-dimethylocta-2,6-dien-1,8-diyl)-ruthenium is reacted with 2,4-dimethyl-1,3-pentadiene, in the presence of ethanol, acetonitrile and lithium carbonate to provide bis(2,4-dimethyl-2,4-pentadienyl)-ruthenium or {Ru(DMPD)$_2$}.

Unlike the prior art process, the process of the instant invention makes it possible to prepare compounds (I) in high yields, in many cases above 90%. It can be carried out in simple equipment and it does not require particular temperature or pressure conditions.

EXAMPLES

The invention will now be described in further detail by way of the following examples, in which the temperatures are indicated in degrees centigrade and the abbreviations have the meaning usual in the art.

Example 1

Preparation of {Ru(2,4-dimethyl-2,4-pentadienyl)$_2$}

{RuCl$_2$(2,7-dimethyl-2,6-octadien-1,8-diyl}$_2$ (3.8 g, 6.16 mmol) and Li$_2$CO$_3$ (8.8 g, (119 mmol) were suspended in a mixture of EtOH (150 ml), MeCN (0.33 ml), and 2,4-dimethyl-1,3-pentadiene (4.6 g, 48 mmol), and the resulting mixture was stirred at reflux for 5 h. The low-boiling volatiles were removed on a rotary evaporator, the residue was extracted with CH$_2$Cl$_2$, the extract filtered and concentrated, and the resulting residue purified by sublimation (10$^{-3}$ bar, 80° C.).

Yield 93% (3.36 g, 11.5 mmol, yellow crystals).

$^1$H-NMR(250 MHz, C$_6$D$_6$): δ=4.63(s, 2H, H-3); 2.71(s, 4H, H-1$_{exo}$); 1.73(s, 12H, H-4); 0.86(s, 4H, H1$_{endo}$).

$^{13}$C-NMR(62.9 MHz, C$_6$D$_6$): δ=100.3(C-2), 97.8(C-3), 46.8(C-1), 26.3(C-4).

Example 2

Preparation of {Ru(2,4-cycloheptadienyl)$_2$}

{RuCl$_2$(2,7-dimethyl-2,6-octadien-1,8-diyl}$_2$ (0.31 g, 0.5 mmol) and Li$_2$CO$_3$ (0.15 g, 2.0 mmol) were suspended in a mixture of EtOH (10 ml), MeCN (26 μl, 0.5 mml), and 1,3-cycloheptadiene (0.94 g, 10 mmol), and the resulting mixture then processed as described in Example 1.

Yield 80% (0.23 g, 0.80 mmol).

$^1$H-NMR(250 MHz, C$_6$D$_6$): δ (ppm)=5.01(t, 2H, H-1); 4.37(dd, 4H, H-2); 3.88(m, 4H, H-3); 215, 166(m, 8H, H-4).

$^{13}$C-NMR(62.9 MHz, C$_6$D$_6$): δ (ppm)=94.56(C-1), 88.21 (C-2), 64.88(C-3), 34.95(C-4).

Example 3

Preparation of {Ru(2,3,4-trimethyl-2,4-pentadienyl$_2$}

2,3,4-Trimethylpenta-1,3-dien (0.33 g, 3.0 mmol) was used instead of 1,3-cycloheptadiene and the reaction carried out in a manner similar to that described in the preceding examples.

Yield 62% (0.20 g, 63%).

$^1$H-NMR(250 MHz, C$_6$D$_6$): δ=2.73(s, 4H, H-1$_{exo}$); 1.53 (s, 12H, H-4); 1.46(s, 6H, H-5); 0.86(s, 4H, H-1$_{endo}$).

$^{13}$C-NMR(62.9 MHz, C$_6$D$_6$) : δ=105.9(C-3); 96.26(C-2); 49.0(C-1); 25.2(C-4); 16.4(C-5).

What is claimed is:

1. A process for the preparation of ruthenium compounds of the formula $$\{Ru(dienyl)_2\} \quad (I)$$

wherein "dienyl" represents a substituted pentadienyl or cycloheptadienyl group, which process comprises reacting dichloro(2,7-dimethylocta-2,6-dien-1,8-diyl)-ruthenium with an appropriate diene in the presence of sufficient amounts of: (1) a primary or secondary alcohol capable of reducing Ru(IV) to Ru(II); and (2) a carbonate of an alkaline material, and under reaction conditions sufficient to form Ru(dienyl)$_2$.

2. The process of claim 1, wherein the reaction takes place in the presence of a catalytic amount of acetonitrile.

3. The process of claim 1, wherein the compound of formula (I) comprises a 2,4-dimethyl-2,4-pentadienyl, 2,3,4-trimethyl-2,4-pentadienyl, 2,4-dimethyl-1-oxa-2,4-pentadienyl, or 2,4-cycloheptadienyl group.

4. The process of claim 1, wherein the alcohol is ethanol or methanol.

5. The process of claim 1, wherein the carbonate is lithium carbonate.

6. The process of claim 1, wherein the dichloro(2,7-dimethylocta-2,6-dien-1,8-diyl)-ruthenium is reacted with 2,4-dimethyl-1,3-pentadiene in the presence of effective amounts of ethanol, acetonitrile and lithium carbonate to provide bis(2,4-dimethyl-2,4-pentadienyl)-ruthenium.

7. The process of claim 1, wherein the alcohol and carbonate are present in amounts sufficient to obtain a high yield of Ru(dienyl)$_2$ of about 90%.

* * * * *